US00PP13632P2

(12) United States Plant Patent
van Gaalen

(10) Patent No.: US PP13,632 P2
(45) Date of Patent: Mar. 11, 2003

(54) PHLOX PLANT NAMED 'RED FEELINGS'

(76) Inventor: Irenaeus A. M. van Gaalen, Noordhoornseweg 37, 2635 GC Den Hoorn (NL)

( * ) Notice: Subject to any disclaimer, the term of this patent is extended or adjusted under 35 U.S.C. 154(b) by 0 days.

(21) Appl. No.: 09/984,576

(22) Filed: Oct. 30, 2001

(51) Int. Cl.[7] ..... A01H 5/00
(52) U.S. Cl. ..... Plt./320
(58) Field of Search ..... Plt./320

(56) References Cited

PUBLICATIONS

UPOV–ROM GTITM Computer Database 2001/01, GTI JOUVE Retrieval Software, citation(s) for 'Red Feelings' Feb. 6, 2001.*

* cited by examiner

*Primary Examiner*—Bruce R. Campell
*Assistant Examiner*—A Para
(74) *Attorney, Agent, or Firm*—Foley & Lardner

(57) ABSTRACT

A new and distinct cultivar of Phlox plant named 'Red Feelings', characterized by its upright plant habit; panicles of reddish purple persistent inflorescences that do not shed.

3 Drawing Sheets

LATIN NAME OF THE GENUS AND SPECIES OF THE PLANT CLAIMED

*Phlox paniculata.*

VARIETY DENOMINATION

'Red Feelings'.

BACKGROUND OF THE INVENTION

The present invention relates to a new and distinct cultivar of Phlox plant of the family Polemoniaceae, botanically known as *Phlox paniculata*, and hereinafter referred to by the cultivar name 'Red Feelings'.

The new cultivar is a whole plant mutation from Phlox 'Bright Eye Elite' (unpatented) in Den Hoorn, The Netherlands. 'Red Feelings' was discovered and selected by the inventor, Irenaeus A. M. van Gaalen, in October 1999, in Den Hoorn, The Netherlands.

'Red Feelings' is a product of a planned breeding program conducted by the Inventor and selected in a cultivated environment in Den Hoorn, The Netherlands. Asexual reproduction of the new cultivar by tissue culture was first performed in June, 2000, in Maasdijk, The Netherlands. Asexual reproduction of the new cultivar by cuttings was first performed January, 2001, in Den Hoorn, The Netherlands, and has demonstrated that the combination of characteristics as herein disclosed for the new cultivar are firmly fixed and reproduce true to type in successive generations of asexual reproduction.

BRIEF DESCRIPTION OF THE INVENTION

The following traits have been repeatedly observed and are determined to be basic characteristics of 'Red Feelings' which in combination distinguish this Phlox as a new and distinct cultivar:

1. reddish purple inflorescence color;
2. inflorescences that do not have typical Phlox flowers;
3. persistent inflorescences that do not shed; and
4. upright plant habit.

'Red Feelings' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Den Hoorn, The Netherlands, in a glass greenhouse under average daytime temperatures of 18 to 32 degrees Celsius and nighttime temperatures of 10 to 18 degrees Celsius. No artificial lighting, photoperiodic treatments or other cultural or environmental treatments are conducted, no growth retardants are added. These conditions closely approximate those generally used in commercial practice.

Highest temperature resistant is unknown but known tolerance is up to 30 degrees Celsius. The lowest temperature tolerance is unknown, but known tolerance is to USDA Zone 6.

The amount of time needed to produce a flower from a rooted cutting is 30 weeks. It takes 12 months to produce a commercial plant from tissue culture. The flowers have a tenability of up to 10 to 14 day on average, and 10 days on average as a cut flower. The plants are field grown or in grown in 1.5 liter containers.

Of the many commercial cultivars known to the present inventor, the most similar in comparison to 'Red Feelings' is the cultivar 'Natural Feelings' (U.S. Plant patent application Ser. No. 09/984,538). The flowers of 'Natural Feelings' are green, white, and pink, whereas the flowers of 'Red Feelings' are reddish purple. The flower shape of 'Natural Feelings' resembles that of a small flower, whereas the flower shape of 'Red Feelings' are less developed than a small flower. The inflorescence of 'Natural Feelings' have more flowers than the inflorescence of 'Red Feelings'.

In comparison to Phlox paniculata 'Bright Eye Elite' (unpatented), from which 'Red Feelings' is a mutant, 'Bright Eye Elite' has normal *Phlox paniculata* flowers while 'Red Feelings' has much smaller flowers with different flowers. 'Bright Eye Elite' has dark pink to light pink flowers that are 3.5 to 4 cm in length, while the flowers of 'Red Feelings' are reddish purple and 1.2 cm in length. In general, the stem, leaves, and roots of 'Bright Eye Elite' and 'Red Feelings' are the same.

BRIEF DESCRIPTION OF THE DRAWING

The accompanying photographic drawings show typical plants of Phlox 'Red Feelings' with colors as accurate as is possible with photographic drawings of this type.

The first drawing depicts a close-up of the inflorescence of 'Red Feelings'.

The second drawing shows the inflorescence of 'Red Feelings'.

The third drawing shows a plant of 'Red Feelings'.

DETAILED BOTANICAL DESCRIPTION

The following observations, measurements and values describe the new cultivar at 24 months of age as grown in Den Hoorn, The Netherlands, in 2000 and 2001 under conditions which closely approximate those generally used in commercial practice.

Color references are made to The Royal Horticultural Society Colour Chart (R.H.S.), except where general colors of ordinary significance are used. Color values were taken under daylight conditions at approximately noon in Boskoop, The Netherlands.

Propagation:
- *Type cutting.*—Tissue culture.

Plant:
- *General appearance and form.*—Herbaceous perennial, conical in shape.
- *Height.*—70 cm.
- *Width.*—40 cm.
- *Growth habit.*—Upright.
- *Winter hardiness.*—The lowest temperature tolerance is unknown but at least hardy to USDA Zone 6.
- *Plant vigor.*—Moderate, in spring approximately 15 cm per month, depending on growing conditions.
- *Rooting habit.*—Freely branching.
- *Blooming habit.*—Once a year, continuously, on average four harvestable stems per year (young plant).
- *Blooming period.*—Summer, June–August.
- *Branching habit.*—Moderate; main shoots appear from base, the panicles are branched.
- *Number of lateral branches.*—Only the panicles are branched, average 8.
- *Lateral branch length.*—Average 4 cm.
- *Lateral branch diameter.*—Average 1.5 mm.
- *Internode length.*—Average 4 cm.

Stem:
- *Appearance shape.*—Rounded, glabrous, slightly shiny.
- *Aspect.*—Circular.
- *Strength.*—Strong.
- *Color.*—Green; RHS 143 A.
- *Pubescence.*—None.

Foliage:
- *Arrangement.*—Opposite.
- *Type.*—Single.
- *Color.*—Immature leaves: Upper side green RHS 137 A to 139 A; under side green RHS 137 C. Mature leaves: Upper side green RHS 137 A, under side green RHS 138 A to RHS 138 B.
- *Length.*—Average 11 cm.
- *Width.*—Average 3.1 cm.
- *Shape.*—Elliptic to narrow elliptic.
- *Apex.*—Acute.
- *Base.*—Attenuate.
- *Margin.*—Very finely serrate.
- *Texture.*—Smooth and glabrous on both sides, no pubescence.
- *Venation pattern.*—Pinnate.
- *Quantity.*—Main branches have 24 (12 pairs) of leaves on average.
- *Midrib color.*—Upper and under sides green RHS 143 C to RHS 144A.

Petioles:
- *Color.*—Green, RHS 143 C.
- *Size.*—Average length is 2 mm; average diameter is 4.5 mm; average height is 2.5 mm.

Venation pattern: Pinnate.

Flowers:
- *Flower type and habit.*—Typical Phlox flowers do not develop. Panicles with numerous clusters of bract-like structures are present and persistent.
- *Form.*—Single.
- *Borne/arrangement.*—Inflorescence form is panicle, arrangement is terminal panicle.
- *Height.*—Average 17 cm.
- *Width.*—Average 15 cm.
- *Quantity.*—On average over 50 per lateral flowering branch, on average over 50 flower buds per lateral flowering branch, on average over 400 flowers per main stem, on average over 1500 flowers and buds per plant.

Petals:
- *Petal count.*—5.
- *Petal color.*—Upper side: Purple, RHS 79 B to RHS 79 C when opening and when fully opened. Under side: Purple, RHS 79 B when opening and when fully opened.
- *Petal shape.*—Narrow Ovate with lower half fused (tube).
- *Appearance.*—Dull, twisted.
- *Texture.*—Smooth.
- *Arrangement.*—Rotate.
- *Margin.*—Entire.
- *Tip.*—Acute.
- *Length.*—Average 1.5 cm.
- *Width.*—Average 3 mm.
- *Fragrance.*—None.

Sepals:
- *Appearance.*—Smooth, dull.
- *Arrangement.*—Rotate.
- *Number.*—5.
- *Shape.*—Campanulate.
- *Margin.*—Entire.
- *Tip.*—Apiculate.
- *Base.*—Fused into a campanulate structure.
- *Length.*—Average 7.5 mm.
- *Width.*—Base of the tips on average 3.5 mm.
- *Color.*—Immature: Upper side; green, RHS 77 A to RHS 186 A; under side; green; RHS 137 B. Mature: Upper side; purple RHS 77 A; under side, green, RHS 137 B.
- *Flower size.*—Average 1.2 cm in length and 7 mm in diameter.
- *Flower type.*—Single.

Roots: Thick, fibrous development; freely branching; in summer it takes about 20 days at 20 degrees Celsius to produce a rooted cutting; in winter it takes about 35 days at 12 degrees Celsius to produce a rooted cutting.

Reproductive organs:
- *Number of pistils.*—1.
- *Pistil length.*—Average 7 mm.
- *Stigma.*—3-parted stigma, decurrent in shape; yellow-green in color, RHS 145 D.
- *Style.*—Length is 6 mm on average; yellow-green in color, RHS 145 B to RHS 145 C.
- *Ovary.*—Green, RHS 140 A to RHS 140 B.
- *Stamens.*—5 in quantity.

*Pollen.*—Very little production, color RHS 2 C to RHS 2 D.

Seeds:

*Seed development.*—None observed to date.

Disease resistance susceptibility: No observations made.

I claim:

1. A new and distinct Phlox plant named 'Red Feelings', substantially as illustrated and described herein.

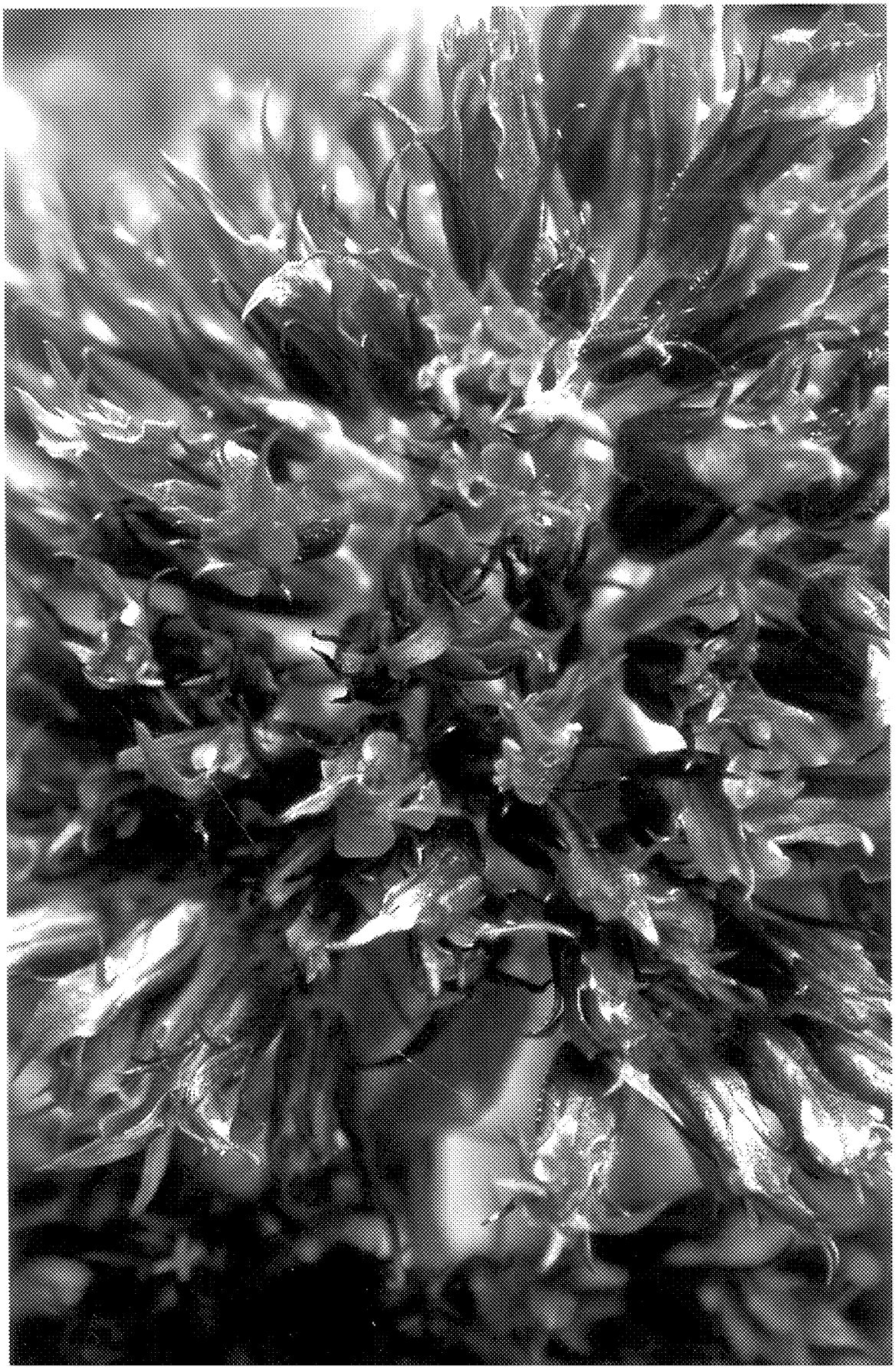

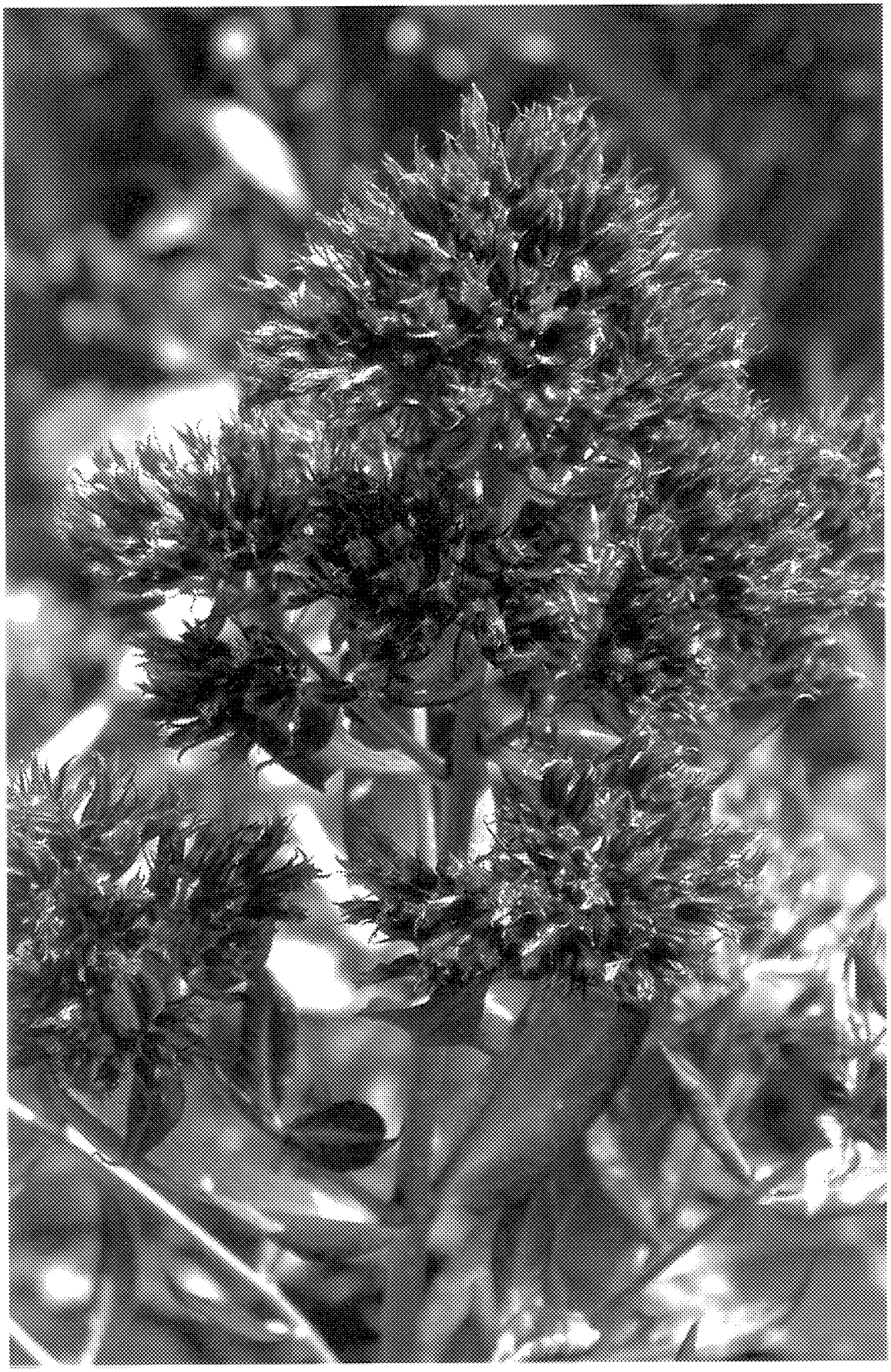

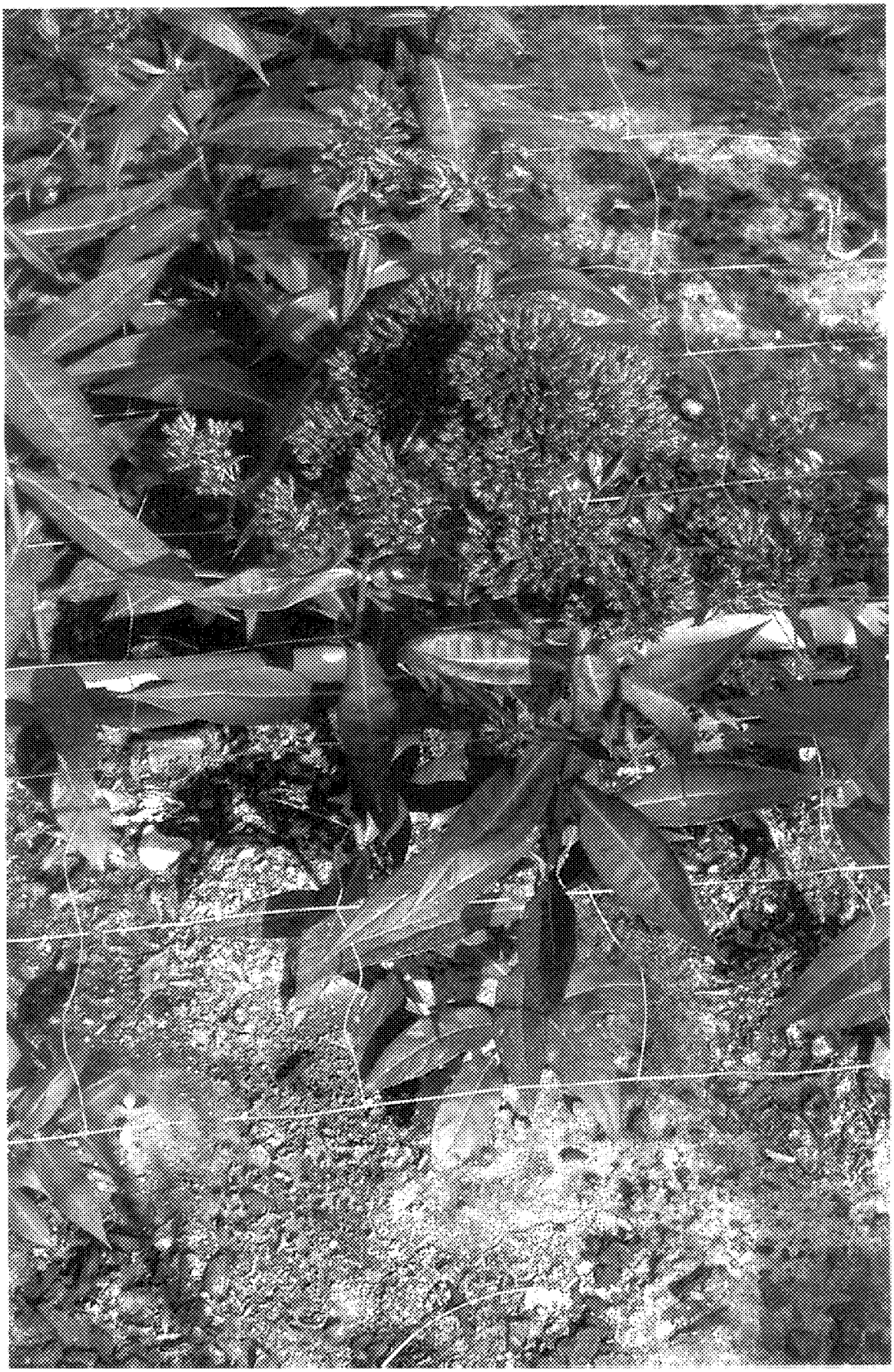

* * * * *